US008633007B2

(12) United States Patent
Petersen et al.

(10) Patent No.: US 8,633,007 B2
(45) Date of Patent: Jan. 21, 2014

(54) DIAGNOSIS OF ENDOMETRITIS

(75) Inventors: Morten Rønn Petersen, Hvidovre (DK); Anders Miki Bojesen, Copenhagen (DK)

(73) Assignee: Kobenhavns Universitet, Copenhagen K (DK)

(*) Notice: Subject to any disclaimer, the term of this patent is extended or adjusted under 35 U.S.C. 154(b) by 3 days.

(21) Appl. No.: 13/140,496

(22) PCT Filed: Dec. 18, 2009

(86) PCT No.: PCT/DK2009/050348
§ 371 (c)(1),
(2), (4) Date: Aug. 26, 2011

(87) PCT Pub. No.: WO2010/069335
PCT Pub. Date: Jun. 24, 2010

(65) Prior Publication Data
US 2012/0058087 A1    Mar. 8, 2012

Related U.S. Application Data

(60) Provisional application No. 61/139,096, filed on Dec. 19, 2008.

(30) Foreign Application Priority Data

Dec. 19, 2008  (DK) ................................ 2008 01821

(51) Int. Cl.
*C12N 1/20*    (2006.01)
(52) U.S. Cl.
USPC ......................................................... 435/243
(58) Field of Classification Search
USPC ......................................................... 435/243
See application file for complete search history.

(56) References Cited

FOREIGN PATENT DOCUMENTS

WO    WO02/45736    6/2002

OTHER PUBLICATIONS

Nau et al. Modulation of release of proinflammatory bacterial compounds by antibacterials: potential impact on course of inflammation and outcome in sepsis and meningitis. Clinical Microbiology Reviews. 2002; 15(1):95-110.*
Alghamdi et al. Equine seminal plasma reduces sperm binding to polymorphonuclear neutrophils (PMNs) and improves the fertility of fresh semen inseminated into inflamed uteri. Reproduction. 2004;127:593-600.*
Fumuso et al. Endometrial IL-1beta, IL-6 and TNF-alpha, mRNA expression in mares resistant or susceptible to post-breeding endometritis effects of estrous cycle, artificial insemination and immunomodulation. Veterinary Immunology and Immunopathology. 2003;96:31-41.*
LeBlanc et al. Use of a low-volume uterine flush for diagnosing endometritis in chronically infertile mares. Theriogenology. 2007;68:403-412.*
Chapwanya et al. Uterine disease in dairy cows: classification, diagnosis and key roles for veterinarians. Irish Veterinary Journal. 2008;61(3):183-186.*
Troedsson et al. Interaction between equine semen and the endometrium: the inflammatory response to semen. Animal Reproduction Science. 2001;68:273-278.*
Alber et al; "Multiplex Polymerase Chain Reaction for Identification and Differentiation of *Streptococcus equi* subsp. *Zooepidemicus* and *Streptococcus equi* subsp. equi". J. Vet. Med. B 51, pp. 455-458 (2004).
Alghamdi et al; "Equine seminal plasma reduces sperm binding to polymorphonuclear neutrophils (PMNs) and improves the fertility of fresh semen inseminated into inflamed uteri", J Reprod Fertil, vol. 127, pp. 593-600, 2004.
Boyd et al; Absorption of neomycin from the equine uterus: effect of bacterial andchemical endometritis. Vet Rec 122, pp. 37-39 (1988).
Båverud et al; "Real-time PCR for detection and differentiation of *Streptococcus equi* subsp. *equi* and *Streptococcus equi* subsp. *Zooepidemicus*", Veterinary Microbiology, 124, pp. 219-229 (2007).
Fiala et al; "Effect of sperm numbers and concentration on sperm transport and uterine inflammatory response in the mare". Theriogenology 67, pp. 556-562 (2007).
Fumuso et al; "Endometrial IL-1beta, IL-6 and TNF-alpha, mRNA expression in mares resistant or susceptible to post-breeding endometritis. Effects of estrous cycle, artificial insemination and immunomodulation", Veterinary Immunology and Immunopathology, vol. 96, No. 1-2, pp. 31-41, Nov. 15, 2003.
Hafner et al; "Vaccines for *Clamydia* infections of the female genital tract", Future Microbiology, 3, pp. 67-77 (2008).
Hinrichs et al; "Evaluation of progesterone treatment to create a model for equine endometritis", Equine Veterinary Journal 23, pp. 457-461 (1992).
Kaufmann et al; "Prevalence of bovine subclinical and its effects on first service conception rate", Theriogenology, vol. 17, No. 2, pp. 385-391, Sep. 17, 2008.
Keep et al; "Wake up! Peptidoglycan lysis and bacterial non-growth states", Trends in Microbiology, 14, 6, pp. 271-276 (2006).
Kotilainen et al; "Sperm-induced leukocytosis in the equine uterus", Theriogenology 41, pp. 629-636 (1994).
Larsen et al; "Re-activation of bovine tuberculosis in a patient treated with infliximab", The European Respiratory Journal: Official Journal of the European Society for Clinical Respiratory Physiology, vol. 32, No. 1, pp. 229-231, Jul. 1, 2008.
Leblanc et al; "Use of a low-volume uterine flush for diagnosing endometritis in chronically infertile mares", Theriogenology, Los Altos, CA, US, vol. 68, No. 3, pp, 403-412, Jul. 5, 2007.

(Continued)

*Primary Examiner* — Ruth Davis
*Assistant Examiner* — Lynn Y Fan
(74) *Attorney, Agent, or Firm* — Gifford, Krass, Sprinkle, Anderson & Citkowski, P.C.

(57)    ABSTRACT

The present invention relates to methods for diagnosing and treatment of a dormant infection of at least one pathogen. The invention further relates to a composition comprising an anti-dormancy factor as well as to said composition for use in a method of diagnosis or treatment and also to a method for manufacturing said composition. The invention further relates to a kit of parts comprising, inter alia, said composition. The invention also relates to a method for activating a dormant infection.

13 Claims, No Drawings

(56) References Cited

OTHER PUBLICATIONS

Lee et al; "Fertilization and Development In Vitro of Bovine Oocytes following Intracytoplasmic Injection of Heat-Dried Sperm Heads", Biology of Reproduction 74, pp. 146-162 (2006).

Lewis, Kim, "Persister cells, dormancy and infectious disease", Nature Microbiology Reviews, 5, pp. 48-56 (2007).

Liu et al; "The diagnosis and treatment of endometritis in the mare: Yesterday and today", Theriogenology, Los Altos, CA, US, vol. 70, No. 3, pp. 415-420, Aug. 1, 2008.

McGinley et al; "Studies on the ability of a 98-kilodalton pseudorabies virus diagnostic antigen to detect latent infections induced by low-dose exposure to the virus", American Journal of Veterinary Research, American Veterinary Medicine Association, vol. 49, No. 9, pp. 1489-1493, Sep. 1, 1988.

Miragaya et al; "Endometritis, salpingitis and fertilisation rates after mating mares with a history of intrauterine lumenal fluid accumulation", Equine Vet. J Suppl 25, pp. 109-112 (1997).

Nielsen, Jesper Møller; "Endometritis in the mare: A diagnostic study comparing cultures from swab and biopsy", Theriogenology, 64, pp. 510-518 (2005).

Nikolapoulos et al; "Effect of infusion volume and sperm numbers on persistence of uterine inflammation in mares", Equine Vet J 32 (2), pp. 164-166 (2000).

Ravagnani et al; "A novel firmicute protein family related to the actinobacterial resuscitation-promoting factors by non-orthologous domain displacement", BMC Genomics, 6:39, pp. 1-14 (2005).

Rohrbach et al; "Effect of adjunctive treatment with intravenously administered Propionibacterium acnes on reproductive performance in mares with persistent endometritis", Journal of the American Veterinary Medical Association, vol. 231, No. 1, pp. 107-113, Jul. 1, 2007.

Stabel et al; "Augmentation of secreted and intracellular gamma interferon following johnin purified protein derivative sensitization of cows naturally infected with *Mycobacterium avium* subsp. paratuberculosis", Journal of Veterinary Diagnostic Investigation, vol. 19, No. 1, pp. 43-51, Jan. 1, 2007.

Traub-Dargatz et al; "Medical problems of adult horses, as ranked by equine practitioners", J Am Vet Med Assoc 198, pp. 1745-1747 (1991).

Troedsson et al; "Components in seminal plasma regulating sperm transport and elimination", Animal Reproduction Science 89, pp. 171-186 (2005).

Watson et al; "Concentrations of immunoreactive leukotriene B4 in uterine lavage fluid from mares with experimentally induced and naturally occuring endometritis", J vet Pharmacol. Therap. 11, pp. 130-134 (1988).

Zerbe, et al; "Development and comparison of in vivo and in vitro models for endometritis in cows and mares", Theriogenology 60, pp. 209-223 (2003).

\* cited by examiner

DIAGNOSIS OF ENDOMETRITIS

CROSS-REFERENCE TO RELATED APPLICATIONS

This application is the U.S. National Phase of PCT/DK2009/050348 filed Dec. 18, 2009, which claims priority of Danish Patent Application PA 2008 01821 filed Dec. 19, 2008 and U.S. Provisional Patent Application 61/139,096 filed Dec. 19, 2008.

All patent and non-patent references cited in the application are hereby incorporated by reference in their entirety.

FIELD OF INVENTION

The present invention relates to methods for diagnosing and treatment of a dormant infection of at least one pathogen. The invention further relates to a composition comprising an anti-dormancy factor as well as to said composition for use in a method of diagnosis or treatment and also to a method for manufacturing said composition. The invention further relates to a kit of parts comprising, inter alia, said composition. The invention also relates to a method for activating a dormant infection.

BACKGROUND OF INVENTION

Endometritis, i.e. infection of the inner lining of the uterus, is the most common cause for infertility in the mare. Diagnosis of endometritis is currently performed by culture of recovered material from the uterus, which is subsequently incubated on blood agar plates at 37° C. Following incubation for 24 hours, a variety of bacteria known to cause endometritis in the mare can be detected. However, *Streptococcus zooepidemicus* (*S. zoo*) and *Escherichia coli* (*E. coli*) are by far the bacteria most frequently isolated, together accounting for approximately 80% of the isolated bacteria.

Recent research has indicated that in some cases *S. zoo* infections of the endometrium can be very difficult to diagnose by the currently available diagnostic methods. This results in a large number of false negatives with respect to endometritis. Such false negatives are highly problematic in relation to e.g. breeding, since the negative result of the test may prompt an attempt to make the mare pregnant, e.g. by artificial insemination or live cover. If the pregnant mare does in fact have an un-diagnosed infection capable of causing endometritis, e.g. a false-negative diagnosed infection, such an infection may prevent establishment of the pregnancy or increase the risk of pregnancy loss at some stage during gestation.

It is an aim of the present invention to overcome the above-mentioned problems relating to endometritis. In particular, it is an aim of the present invention to overcome the problem of difficulties in reliably diagnosing endometritis. It is a further aim of the present invention to provide improved methods of diagnosis and treatment of endometritis.

DEFINITIONS

Activation: Activation of a dormant infection means activating the dormant infectious organism constituting said dormant infection by causing them to divide and by causing the rate of their metabolic processes to increase to a normal, non-dormant level.

Active: An active state of an infection is the opposite of a dormant state of an infection, c.f. herein below. The active state is characterized by normal, i.e. non-dormant, rates of metabolic processes and normal, i.e. non-dormant, cellular division.

Anti-dormancy: An anti-dormancy factor is a compound or composition capable of activating a dormant unit, such as a dormant pathogen, such as dormant bacteria, and thereby activating a dormant infection of the dormant unit.

Diagnosis: Diagnosis is the act or process of identifying or determining the nature and cause of a pathological state or condition, such as disease, injury or infection through evaluation.

Dormant: A dormant unit, such as a pathogen, is a viable unit, which has a global but reversible slowdown of metabolic processes and does not divide. Dormant infections are sometimes also known as "latent" or "subclinical" infections. Dormant is an adverb, which can be used both about a specific unit, such as a bacteria, and about a state or condition, such as infection. A dormant infection is an infection with a given unit, such as a bacterium, wherein said unit, e.g. bacterium, is dormant. A dormant bacterium will generally be very difficult to treat and diagnose. For instance, diagnostic tests often rely on there being a large number of units, such as bacteria. Similarly, methods of treatment often rely on the units, such as bacteria, being metabolically active.

Endometritis: Endometritis is an acute or chronic inflammation of the endometrium of the uterus. Endometritis can be caused by microbial infection, but can also arise from non-infectious causes.

Infection: An infection is a colonization of a host organism by a foreign species. For instance, the presence of bacteria in the endometrium of a mammal is an infection by said bacteria. Infection can be dormant or active as further described herein.

Mare: A mare is a female equine, such as a female horse, donkey, ass or zebra.

Pathogen: A pathogen is a biological agent, such as a bacterium, virus or fungus, which causes or is capable of causing disease or illness to its host. In the case of a dormant infection of a pathogen, the pathogen may lie dormant in the host and not cause a pathological condition, such as disease or illness, in its host as long as the pathogen remains dormant. When a dormant pathogen is activated and thereby goes out of dormancy and into its normal active state, the pathogen can cause a pathological condition.

Pro-inflammatory: A pro-inflammatory compound or composition is capable of causing, inducing, promoting or enhancing inflammation in a subject.

Spermatozoa: The term spermatozoa refers to the male reproductive cells. The term is used interchangeably with "sperm". Semen is an organic fluid, also known as seminal fluid, which usually contains spermatozoa.

Treatment: Treatment can be performed in several different ways, including curative, ameliorating and as prophylaxis. Curative treatment generally aims at curing a clinical condition, such as a disease or an infection, which is already present in the treated individual. Ameliorating treatment generally means treating in order to improve in an individual an existing clinical condition. Prophylactic treatment generally aims at preventing a clinical condition.

SUMMARY OF INVENTION

The present invention relates to a method for diagnosing a dormant infection of at least one pathogen in a subject, said method comprising the steps of a. providing a composition comprising a compound selected from the group consisting of an anti-dormancy factor, a pro-inflammatory compound, and a resuscitation-promoting factor,
b. administering said composition to said subject, thereby activating said dormant infection,
c. obtaining a sample from said subject, and
d. subjecting said sample to a diagnostic test in order to detect said pathogen, thereby diagnosing said dormant infection.

The invention further relates to a method for treatment of a dormant infection of at least one pathogen in a subject, said method comprising the steps of
a. providing a composition comprising a compound selected from the group consisting of an anti-dormancy factor, a pro-inflammatory compound, and a resuscitation-promoting factor,
b. administering said composition to said subject, thereby activating said dormant infection,
c. treating said activated infection.

The invention further relates to a method for treatment of a dormant infection of at least one pathogen in a subject, said method comprising the steps of the steps of
   a. performing a diagnosis according to the method of diagnosis of the present invention,
   b. treating said activated infection.

The invention further relates to a composition comprising a compound selected from the group consisting of an anti-dormancy factor, a pro-inflammatory compound, and a resuscitation-promoting factor.

The invention further relates to a said composition for use in a method of diagnosis or treatment of a condition in a subject.

The invention further relates to a kit comprising
   a. a composition according to the present invention, and
   b. instructions for use of said composition.

The invention further relates to a method for manufacturing a composition according to the invention, said method comprising the steps of
   a. rendering the spermatozoa of said composition non-viable, and
   b. rendering the composition aseptic or sterile.

The invention further relates to a method for activating a dormant infection, said method comprising the step of administering to a subject a composition according to the invention, thereby activating said dormant infection.

Preferred embodiments of the invention are set out in the dependent claims.

DETAILED DESCRIPTION OF THE INVENTION

The inventors have demonstrated that certain bacteria, e.g. *S. zoo*, are capable of establishing dormant infections in the endometrium. The inventors have further shown, surprisingly and for the first time, that induction of inflammation in the host can activate dormant infections of e.g. *S. zoo*.

By activation the dormant infection is brought out of dormancy and into an active state. In the active state, the infection will be easier to diagnose and treat. Thus, the activation of said dormant infections enables improved diagnosis and treatment of the infections. The inventors have surprisingly shown, that activation of dormant infections can improve diagnosis drastically leading to earlier and more reliable detection of infection, improved treatment and reduced suffering for the affected individual as well as reduced cost of treatment and economic loss during disease.

The inventors have shown that female horses can carry a dormant infection in the endometrium by *S. zoo* and that the mostly used diagnostic method, the swab test, is unlikely to detect such a dormant infection. The inventors have further shown that the diagnostic sensitivity can be improved drastically by inflammation-assisted diagnostics independent of the diagnostic method used. Furthermore, subsequent antimicrobial treatment will have a considerable higher cure-rate than if applied without prior inflammation induction.

Dormant Infection

Dormancy can be considered as a reversible state of low metabolic activity in a unit that maintains viability. Some pathogens, e.g. bacteria such as *Mycobacterium tuberculosis*, are capable of entering a dormant state during a persisting infection. From a clinical point of view dormant infections are very undesirable since the vast majority of treatments, e.g. antimicrobials, are active only against metabolically active cells.

The inventors have shown that bacteria involved in endometritis are capable of entering a dormant state wherein the bacteria lie dormant in the endometrium of the infected host. Thus, in a preferred embodiment of the present invention, the dormant infection is an infection capable of causing endometritis. The dormant bacteria may reside in several locations of the endometrium or may be localised to one or a few locations. The number of dormant bacteria may vary, but even a relatively low number of dormant bacteria may, upon activation, lead to a pathological state such as endometritis. The fact that the bacteria capable of causing endometritis lie dormant in the host makes it very difficult to effectively and reliably diagnose and treat the dormant infection.

Agent

A large number of different agents, e.g. microbes such as bacteria, fungi or yeasts, may cause dormant infections. Preferably, the dormant infection of the present invention is a streptococcal infection of the reproductive tract. The inventors note that bacteria from the same genus, e.g. *Streptococcus*, tend to behave similarly in the way they interact with their host. As can be seen from Table 1, streptococci are very common inhabitants of the reproductive tract where they can cause a localized infection, which rarely will disseminate systemically. In addition, offspring born by an infected individual are also at risk of getting infected during passage through the birth canal. Also, some of the streptococcal species have been demonstrated able of causing dormant infections. This ability may apply to a wider range if not all reproductive tract associated streptococci. A number of non-streptococcal bacterial agents have been identified in relation to reproductive tract infections, some of which have been demonstrated able of entering a dormant state too.

Condition/Indication

A number of different clinical conditions or indications can be caused by a dormant infection when said dormant infection is activated. Preferably, the present invention relates to dormant infection capable of causing endometritis, vaginitis or cervicitis. Physiologically, endometritis, vaginitis and cervicitis are related conditions. In many instances, an untreated endometritis can spread to the cervix and vagina, thereby giving rise also to cervicitis and vaginitis. Similarly, vaginitis can spread to the cervix and endometrium and cervicitis can spread to the vagina and endometrium.

Endometritis is an acute or chronic inflammation of the endometrium of the uterus. Endometritis can be caused by microbial infection, such as a dormant infection becoming active, but can also arise from non-infectious causes. Endometritis can arise in many different hosts, e.g. mares, horses, cows, dogs, cats, and humans. Endometritis is a contributing factor to infertility. Acute Endometritis is characterized by infection. Chronic Endometritis is characterized by the presence of plasma cells in the stroma. The most common causes of endometritis in humans are chronic pelvic inflammatory disease (PID), tuberculosis, and chlamydiosis. Symptoms of endometritis include lower abdominal pain, fever, and abnormal vaginal bleeding or discharge. Treatment of endometritis is usually with antibiotics. Treatment of endometritis in the mare can also be by lavage or ecbolic agents.

Vaginitis is an inflammation of the vaginal mucosa and often associated with an irritation or infection of the vulva, thus leading to vulvovaginitis. Vaginitis is a common problem in humans and horses. The typical symptoms include irritation and/or itching of the genital area, inflammation (irritation, redness, and swelling caused by the presence of extra immune cells) of the labia majora, labia minora, or perineal area, vaginal discharge, foul vaginal odour, discomfort or burning when urinating, and pain/irritation with sexual intercourse. Vaginitis can for instance be caused by infection, such as a dormant infection becoming active. Treatment of vaginitis depends upon the cause of the condition, Bacterial vaginitis is typically treated with antibiotics.

Cervicitis is inflammation of the tissues of the cervix. Cervicitis can be caused by a number of different infections, such as chlamydia and gonorrhoea.

Host

Dormant infections, such as a dormant infection capable of causing endometritis, can exist in a wide variety of different hosts. Non-limiting examples of hosts are mammals, such as cat, dog, pig, cow, camelids, donkey, horse; non-mammals e.g. poultry, chicken, duck, turkey; endangered animals; non-human primates and humans. In a preferred embodiment of the present invention, the host of the dormant infection is a female equine, more preferably a female horse. In another embodiment, the host is a female human. Endometritis is a major cause of infertility. Thus, the treatment of dormant infections capable of causing endometritis can raise fertility, prevent infertility or reduce infertility in the treated individual. This is particularly relevant for individuals undergoing breeding, in vitro fertilization, artificial insemination, or assisted fertilization. In particular, horse breeding is a major business wherein large sums of money are routinely paid to obtain semen from a particular stallion, either as live covering of the mare or as semen for use in insemination. By the improved diagnosis and treatment provided by the present invention, the risk of the mare developing endometritis after having been inseminated or covered is reduced. This leads to a decreased risk of complications during establishment of pregnancy and in particular a decreased risk of spontaneous abortion. Thus, the chance of getting the mare pregnant as fast as possible and obtaining a live foal is increased. This is obviously of great value to horse breeders since the chances of producing a foal per mare each year is increased and the amount of money spent on repeated inseminations can be reduced or eliminated. Also, the physical discomfort and suffering of the horse resulting from complications caused by endometritis can be reduced or eliminated.

Dormant infections are a problem in humans. Dormant infections may also be a problem in relation to genital tract infections in humans. In particular, endometritis and/or vaginitis can be a problem in relation to pregnancy, and improved diagnosis and treatment of dormant infections capable of causing endometritis and/or vaginitis in women would be highly advantageous. In addition, since offspring born by an infected individual are also at risk of getting infected during passage through the birth canal, diagnosis and treatment of a dormant infection is indicated to minimize the risk of infection in the newborn. The importance of this is underlined by the fact that streptococcal infections are the main reason for infectious abortion in humans and infection in the newborn. Especially in relation to assisted fertilization and in vitro fertilization, reducing the risk of complications during establishment of pregnancy and abortion is advantageous.

Endometritis can especially be a problem in older mares. The method described herein may thus be used for all mares capable to be breed. Preferred is when the mares are at least 5 years old. More preferred the mares are at least 6 years old. Further preferred the mares are at least 7 years old. Yet more preferred the mares are at least 8 years old. Most preferred the mares are at least 9 years old.

In Table 1 herein below includes examples of a range of streptococcal species and the hosts they cause infections in. In many instances, especially with regards to the veterinary field, a number of publications report conditions caused by haemolytic streptococci without further specification as to species designation. These conditions may be caused by known streptococcal species, but may also represent new species. More importantly, in most instances, the clinical conditions are similar to those described in cases caused by known streptococci.

TABLE 1

Causative agents, indications, hosts of infections and observed clinical conditions

| Agent | Condition/Indication | Host | Observed clinical conditions |
|---|---|---|---|
| Streptococcus equi subsp. zooepidemicus | Vaginitis/ endometritis | Horse | Neonatal infections. |
| Streptococcus equi subsp. zooepidemicus | Vaginitis/ endometritis | Dog | Neonatal infections. |
| Streptococcus equi subsp. zooepidemicus | Vaginitis/ endometritis | Camelids | Neonatal infections. |
| Streptococcus agalactiae | Vaginitis/ endometritis | Human | Neonatal septicaemia |
| Streptococcus agalactiae | Meningitis | Human | Neonates |
| Streptococcus agalactiae | Pneumonia | Human | Neonates |
| Streptococcus agalactiae | Vaginitis/ endometritis | Dog | Neonatal septicaemia |
| Streptococcus agalactiae | Vaginitis/ endometritis | Cat | Neonatal septicaemia |
| Streptococcus pyogenes | Vaginitis/ endometritis | Human | Puerperal fever, toxic shock-like syndrome |
| Streptococcus uberis | Mastitis | Cows | |
| Streptococcus canis | Vaginitis/ endometritis | Dog | Neonatal septicaemia |
| Streptococcus canis | Vaginitis/ endometritis | Cat | Neonatal septicaemia |
| Streptococcus acidominimus | Vaginitis/ endometritis | Human | Endometritis and/or vaginitis |
| Streptococcus acidominimus | Vaginitis/ endometritis | Cows | Endometritis and/or vaginitis |

In a preferred embodiment, the present invention concerns improved diagnosis and treatment of dormant infection caused by S. zoo in the endometrium of the mare.

Activation of Dormant Infections

The inventors have shown that dormant infections can be activated by means of administering to the host an anti-dormancy factor, a pro-inflammatory factor, or a resuscitation-promoting factor. Preferably, an anti-dormancy factor is used. More preferably, a pro-inflammatory compound is used. Most preferably, a resuscitation-promoting factor is used.

The finding by the present inventors that a pro-inflammatory compound can be used as an activator of a dormant infection is highly surprising and anti-intuitive. Pro-inflammatory compounds cause inflammation in the host. However, that this inflammation leads to activation of dormant pathogens, and thereby to activation of a dormant infection, has not been previously demonstrated.

Pro-inflammatory compounds that can be used in the present invention include, but are not limited to, spermatozoa, processed spermatozoa, non-viable spermatozoa, IL-1, IL-6, IL-8 (Zerbe et al. 2003), TNF-α, leukotrienes, oil emulsions, polymers, alums, saponins, liposomes, ISCOMs (immunostimulating complexes), Lugols iodine, phosphate buffered saline, glycogen, oyster glycogen, *Eschericia coli*, *Pseudomonas aeruginosa*, lipopolysaccharides, Mycobacterial cell wall components, adjuvants, Freund's complete adjuvant, and Freund's incomplete adjuvant. Lugols iodine can be administered as a 10% solution in 30 ml (Boyd and Allen, 1988). In an embodiment, phosphate buffered saline is used (Kotilainen et al., 1994). Glycogen can be administered as a 1% solution (Miragaya et al., 1997). Oyster glycogen can be administered as a 1% solution (Watson et al., 1988).

IL-8 has been demonstrated to be able of attracting polymorph nuclear neutrophil granulocytes (PMNs) into the uteri of the treated subjects, thus indicating an ability of promoting an inflammatory response. Likewise, other pro-inflammatory substances like IL-1 and TNF-α can lead to activation of dormant infections.

A resuscitation-promoting factor (Rpf) has been described in *Micrococcus luteus* (Keep et al. 2006). Rpf has been demonstrated to be extremely potent at activating dormant micrococci. Homologous proteins have been identified in a number of other bacterial species including the stationary phase survival (SPS) factors identified in several firmicutes (Ravagnani et al., 2005). Rpf and its homologues may also be employed as activators of dormant infections in the present invention. Rpfs are expected to be present in *Mycobacterium tuberculosis* and other GC-rich bacteria. Thus Rpf isolated from GC-rich bacteria e.g. from *Micrococcus luteus* and/or from *Mycobacterium tuberculosis* may be used in an induction composition as described elsewhere herein. Also non-viable or processed bacteria e.g. of *Micrococcus luteus* and/or from *Mycobacterium tuberculosis* can be used as ingredients of the induction composition. Stationary phase survival (SPS) factors may also be employed as activators of dormant infections in the present invention.

In an embodiment the pro-inflammatory compound is selected from the group consisting of processed non-viable spermatozoa, IL-8, non-viable or processed bacteria e.g. processed bacterial known to produce a Rpf-like factor including *Micrococcus luteus* and *Mycobacterium tuberculosis*.

Preferably, the pro-inflammatory compound of the present invention is spermatozoa. The spermatozoa may be from any species. Preferably, the spermatozoa are from boar, bull, or stallion. More preferably, when for use in a mare, the spermatozoa are from a stallion. In an embodiment of the present invention, the spermatozoa are from the same species or a closely related species as the host to which the spermatozoa are to be administered. Closely related species in this context means species where cross-fertilization is possible, e.g. horses and donkeys. In another embodiment, the spermatozoa are from a different species than the host to which the spermatozoa are to be administered. When the spermatozoa are from the same or a closely related species, it is preferable that the spermatozoa are sterile in terms of fertility, since this avoids the potential risk of causing a pregnancy in the host. When the spermatozoa are from a different species, where cross-fertilization is not possible, it is not important that the spermatozoa are sterile in terms of fertility. In other words, a composition of live spermatozoa could be used, as long as the spermatozoa are not capable of causing a pregnancy in the host. This would for instance be the case when using hog spermatozoa in a mare, such as a female horse. It would still be preferable to use sterile spermatozoa in terms of infectivity, i.e. a composition of spermatozoa which does not comprises infectious agents, such as bacteria, fungi or yeast. In a preferred embodiment, spermatozoa are used, wherein said spermatozoa are not capable of causing a pregnancy in the host to which they are administered. An advantage of using spermatozoa as an anti-dormancy factor is that the spermatozoa represent a complex mixture of compounds and that they are therefore capable of eliciting in the host a broad-spectrum immune reaction leading to a broad inflammatory response. The broad inflammatory response is desirable when trying to activate a dormant infection. Furthermore, spermatozoa are a natural product, which the host is used to being exposed to. This means that the risk for adverse reaction is minimal. This is in particular so in relation to endometritis, vaginitis and cervicitis, where the spermatozoa are administered to the uterus or vagina. Also, spermatozoa are cheap and easy to obtain.

The spermatozoa should preferably be sterile, both in terms of fertility and in terms of infectivity. Fertility-wise, the use of sterile sperm, such as killed or damaged sperm, eliminates the risk of the sperm actually fertilizing the subject being exposed to the sperm. In regard to the present invention, the purpose of administering the sperm is not to cause a pregnancy, but to activate a dormant infection. It will therefore generally be an undesirable side-effect to cause a pregnancy when administering the sperm. However, there may be special instances when administration of sperm in the context of the present invention is intended to actually cause a pregnancy. In terms of infectivity, it is desirable to use sterile sperm in order to avoid causing a new infection in the subject to which the sperm is administered. The purpose of administering the sperm is to activate a dormant infection, and it is generally undesirable to cause a new infection at the same time as activating an existing dormant infection. However, there may be special instances when it is preferable to use an infectious agent as an anti-dormancy factor.

The spermatozoa employed in the present invention may for instance have been pre-treated by freeze-thaw cycling, heat treatment for example using an autoclave (autoclavation), chemical inactivation, alcohol treatment, formaldehyde treatment, freeze-drying, convective drying, dehydration in a high-osmolarity medium, or heat drying. Heat treatment of spermatozoa can be performed at temperatures above 70° C., preferably above 80° C., more preferably above 90° C., yet further preferably above 100° C., most preferably above 120° C. The autoclavation can be carried out at a temperature of 121° C. and a pressure of 15 psi. For further details on heat drying procedures refer to Lee and Niwa (2006). The freezing step of the freeze-thaw cycling can preferably be carried out at −18° C.

Preferably, inflammation can be induced by inoculation of dead equine spermatozoa, which have been frozen and thawed prior to inoculation. The number of spermatozoa used is preferably around 1 billion, although other amounts can also be used. The spermatozoa can for instance be administered in sterile phosphate buffered saline (PBS), for instance in a volume of 10 ml. Other volumes can also be used. Before inoculation, the samples of spermatozoa are preferably tested negative for presence of bacteria. Centrifugation can be used to remove seminal plasma and the spermatozoa can be resuspended. Thus, preferably the anti-dormancy solution does not contain seminal plasma. The advantage of removing seminal plasma lies in, that it has been shown to sometimes down-regulate the inflammatory response of the uterus after insemination. This is generally not desirable in the present invention, since the aim is to activate a dormant infection by inducing inflammation in the host. Slow freeze-thaw (−18° C.) of spermatozoa without cryoprotectants can be employed and will induce membrane damage and kill spermatozoa. Killed spermatozoa have an increased ability to induce an inflammatory response in the uterus compared to live. Also, using the killed spermatozoa eliminates the risk of causing a pregnancy. Sterile killed spermatozoa without seminal plasma is therefore preferably used as an anti-dormancy factor to induce inflammation in the host and thereby activate any dormant infections by dormant pathogens.

The sterile spermatozoa can be held in a low volume container. When placed in the low volume container the spermatozoa is sterilized using gamma rays followed by freeze drying. This is to ensure that no microorganisms or fertile sperm cells are introduced into the subject treated with the kit. From quality-control purposes, a subset of every batch of ready-to-use containers can be randomly chosen and evaluated for the presence of live bacteria or spermatozoa. When induction of inflammation is wanted, the sterile spermatozoa can be aspirated in a syringe and deposited in the uterus using standard insemination techniques. Prior to use, the freeze-thawed spermatozoa can be "made fluent" by re-suspension. This approach is often used in vaccines.

The composition may comprise non-viable spermatozoa in an amount of from 1 million to 10 billion spermatozoa cells, such as from 1 million to 100 million, or from 100 million to 200 million, or from 200 million to 300 million, or from 300 million to 400 million, or from 400 million to 500 million, or from 500 million to 600 million, or from 600 million to 700 million, or from 700 million to 800 million, or from 800 million to 900 million, or from 900 million to 1 billion, or from 1 billion to 1.5 billion, or from 1.5 billion to 2 billion, or from 2 billion to 2.5 billion, or from 2.5 billion to 3 billion, or from 3 billion to 3.5 billion, or from 3.5 billion to 4 billion, or from 4 billion to 4.5 billion, or from 4.5 billion to 5 billion, or from 5 billion to 5.5 billion, or from 5.5 billion to 6 billion, or from 6 billion to 6.5 billion, or from 6.5 billion to 7 billion, or from 7 billion to 7.5 billion, or from 7.5 billion to 8 billion, or from 8 billion to 8.5 billion, or from 8.5 billion to 9 billion, or from 9 billion to 9.5 billion, or from 9.5 billion to 10 billion.

The numbers of non-viable spermatozoa as mentioned just above, may be present in a composition and the non-viable spermatozoa can thus be administered to the subject. The composition to be administered to a subject may have a volume of from 1 ml to 50 ml, such as from 1 ml to 5 ml, such as from 5 ml to 10 ml, such as from 10 ml to 15 ml, such as from 15 ml to 20 ml, such as from 20 ml to 25 ml, such as from 25 ml to 30 ml, such as from 30 ml to 35 ml, such as from 35 ml to 40 ml, such as from 40 ml to 45 ml, such as from 45 ml to 50 ml. The volumes of the composition just mentioned may comprise the numbers of non-viable spermatozoa mentioned above.

The composition can have a pH value of from 5 to 9, such as from 5.5 to 8.5, such as from 6 to 8, such as from 6.5 to 7.5, such as from 7 to 7.5, such as from 7.25 to 7.5. Preferably the composition has a physiological pH value.

The composition can have an osmolarity of from 1 mOsm/liter to 1000 mOsm/liter, such as from 50 mOsm/liter to 950 mOsm/liter, such as from 100 mOsm/liter to 900 mOsm/liter, such as from 150 mOsm/liter to 850 mOsm/liter, such as from 200 mOsm/liter to 800 mOsm/liter, such as from 250 mOsm/liter to 750 mOsm/liter, such as from 300 mOsm/liter to 700 mOsm/liter, such as from 350 mOsm/liter to 650 mOsm/liter, such as from 400 mOsm/liter to 600 mOsm/liter, such as from 450 mOsm/liter to 550 mOsm/liter, such as from 500 mOsm/liter to 550 mOsm/liter.

When the host of the dormant infection is a mare, such as a female horse, stallion spermatozoa are preferably used as the pro-inflammatory anti-dormancy factor. The spermatozoa have preferably been subjected to a freeze-thaw cycle in order to damage the spermatozoa to increase the inflammatory response of the uterus of the mare. Using semen or spermatozoa from a homologous species has the immediate advantage of being a "natural" compound in the area of exposure, which is unlikely to cause adverse side effects. Other substances can be used, e.g. Rpf's, pro-inflammatory cytokines, alarmins or other immunoregulatory factors. An advantage of the latter is a better ability of standardizing the level of inflammation induced. However, at least for veterinary application, this is not expected to be a major constrain.

There are several advantages from using damaged or killed spermatozoa, preferably freeze-damaged spermatozoa, as an anti-dormancy factor. Firstly, the inventors have demonstrated that damaged or killed spermatozoa are able of activating dormant infections, such as dormant streptococcal infections, in the uterus of the subject, such as the mare or female horse. Secondly, spermatozoa are composed of a wide spectrum of different proteins and carbohydrates and therefore likely of inducing a broad spectrum immune response. In contrast, if a single protein was used, the immune response elicited may be narrow spectrum and not lead to the same kind of broad inflammatory reaction. Although spermatozoa represent a complex compound, it is intermittently naturally present in the reproductive tract and therefore unlikely to cause any major adverse effects. Finally, damaged or killed spermatozoa, such as freeze-damaged spermatozoa, are very easy to obtain at a low cost, making them a very attractive alternative to native or recombinant proteins that have to be produced, purified and quantified before they can be used.

Spermatozoa can be collected from a stallion using an artificial vagina with an inline filter to remove the gel fraction (third fraction of the ejaculate). Following collection, the concentration of spermatozoa (millions per ml.) in the ejaculate is determined. The ejaculate is typically placed in a temperature and pressure resistant vial, e.g. a glass vial, intended for autoclaving, freeze-drying, heat drying, or other procedure dependent on the decided method. Preferably, a total of around $10^9$ spermatozoa are placed in each vial. Following the above-mentioned damaging or killing procedures, the spermatozoa can no longer fertilize in vivo since the cell membranes are non-intact. Furthermore, no viable microorganisms will be present in the sample. Preferably, the cell membrane of the spermatozoa are destroyed by slow freezing and thawing (−18° C., without cryoprotectants).

The preferred volume of the composition to be administered is around 10 ml, although other volumes can be used. This volume should preferably be selected to make sure that a majority of the preparation intended to be deposited in the uterus or vagina will actually be deposited in the uterus or vagina and not lost in the syringe or insemination pipette used, which could be the case if a very small volume was used. If a very large volume is used, i.e. 500 ml, the level of inflammation induced is generally lower than if a smaller volume, e.g. 40 ml, is used (Nikolapoulos and Watson, 2000).

Regarding the number of spermatozoa, in general the more spermatozoa deposited in the uterus the higher inflammatory response until a certain level (level of inflammation evaluated by number of polymorph nucleated neutrophiles (PMN)).

One study identified a higher number of PMN's present in the uterus when mares were inseminated with $1 \times 10^9$ spermatozoa compared to 100 or $500 \times 10^6$ (Fiala et al., 2007), whereas another study identified the same number of PMN's in the uterus following insemination with either $2 \times 10^9$ or $20 \times 10^9$ spermatozoa (Nikolapoulos and Watson, 2000). It should be noted that these investigations used populations of spermatozoa in which the majority had intact cell membranes. This is important since spermatozoa with damaged membranes/non viable will induce a stronger uterine inflammatory response than spermatozoa with an intact cell membrane/viable (Troedsson et al., 2005). In addition, the seminal plasma (fluid fraction of an ejaculate) modulates the inflammatory response of the uterus following insemination (Troedsson et al., 2005). To induce a strong inflammatory in the uterus an inseminate should therefore preferably be composed of non-viable spermatozoa and no seminal plasma (Alghamdi et al., 2004). In the present invention, $1 \times 10^9$ non-viable spermatozoa without seminal plasma was used with good effect to induce uterine inflammation. Potentially a lower number of non-viable spermatozoa without seminal plasma will induce an adequate level of inflammation.

The overall goal of the spermatozoa is to function as a pro-inflammatory compound without any negative, un-wanted side-effects on the uterus, vagina or cervix of the subject. The composition described herein can thus be administered to the vagina, cervix and/or uterus of a subject. The composition to be inoculated should therefore have a physiological pH value, e.g. approximately pH 7.4. Furthermore, the anti-dormancy factor should preferably be administered as an iso-osmotic solution, e.g. a solution with an osmolarity of approximately 300 mOsm.

The inventors note that the use and positive effect of spermatozoa in connection with the methods of the present invention, e.g. diagnosis and treatment, is both anti-intuitive and surprising. Usually, inflammation caused by spermatozoa, in relation to horses typically termed breeding-induced inflammation, is considered a negative side-effect of live-cover or fertilization.

Diagnosis

Diagnosis of dormant infections is made difficult by the dormancy of the infection. The dormant infection may be localised to a small area of the infected organ, such as the endometrium, and may therefore not be detected by the commonly employed diagnostic tests. For instance, diagnosis by biopsy will only detect the infection if the dormant pathogens happen to be present in the relatively small sample of tissue taken by the biopsy. This will often not be the case with a dormant infection. Similar problems apply to other diagnostic tests. This means that dormant infections are susceptible to a high number of false negative diagnoses. The present inventors have found that dormant infections can be more reliably diagnosed by activating the dormant infection prior to diagnosis, and then diagnosing the resulting active infection. Upon activation, the infection will typically spread to a much larger area of the infected organ, and will therefore be much more likely to be detected by a diagnostic test.

Infections such as endometritis can be diagnosed by several different techniques including bacterial culture from swab, e.g. endometrial swab, biopsy or flushing (Liu and Troedsson, 2008). In addition, a number of techniques can supplement or replace the aforementioned procedures, e.g. cytology, ultrasound detection of uterine fluid as an indication of inflammation, etc. The latter procedures will however merely provide a general indication of endometritis and not enable a specific diagnosis.

The swab is a double-guarded swab, which is guided through the vagina and cervix, released and twisted around in order to cover as large an area of the endometrium as possible. Subsequently, the swab is smeared out on a blood agar plate, which is incubated for 24 hours at 37° C. and subsequently evaluated for bacterial growth.

The endometrial biopsy is obtained by a crocodile biopsy forceps largely by a similar procedure as the swab. However, the biopsy recovers only a tiny area of the endometrium but does so in depth. This means that bacteria located beneath the endometrial lining are more likely of being detected by the biopsy than the swab, which is limited to the endometrial surface (Nielsen, 1985). The biopsy material is also smeared onto a blood agar plate, which is incubated and subsequently evaluated for bacterial growth.

The flushing procedure includes infusion of 50-100 ml sterile, physiological saline into the uterus. An inflatable device prevents the infused liquid from escaping through the cervix and into the vagina. When infused, the saline can be massaged around within the uterus in order for the liquid to cover the entire area of the endometrium. Finally, the liquid is recovered, left to sediment or spun down allowing recovery of the semisolid phase comprising endometrial epithelial cells, immune cells and bacteria. A sample from the semisolid phase is taken out, smeared onto a blood agar plate, incubated and subsequently evaluated for bacterial growth.

In case of bacterial growth, the colonies can be characterized phenotypically, which to a large extend permits initiation of a treatment regiment. If a more detailed identification is needed to assess the bacterial species or subspecies level, additional phenotypic characterization is necessary. Alternatively, genotypic methods can be employed. For instance, for *Streptococcus equi* subspecies *zooepidemicus* or *S. equi* subsp. *equi* identification can be made by conventional PCR (Alber et al., 2004) or by real-time PCR (Båverud et al., 2007). Optionally, the PCR methods can be used directly on the diagnostic samples, e.g. material from swab, flushing or biopsy, thereby bypassing the culturing steps.

Immunologic Competence

The immunologic competence i.e. the ability of cells to mount a humoral or cellular immune response when challenged by antigen may for some reasons be lost e.g. due to repeated infections.

A loss of immunologic competence can be present when a subject has a dormant infection. However, the loss of immunologic competence e.g. in the uterus need not be because of a dormant infection capable of causing endometritis, vaginitis and/or cervicitis.

It is possible to test a subject e.g. a human or animal such as a mare for whether they are immunological competent. This test can be performed by administering to the subject a composition as described elsewhere herein and determine whether neutrophils (white blood cells) can be visualized in a sample obtained from the subject. The presence of no or a low number of neutrophils indicates that the subject is not immunological competent. The presence of a high number of neutrophils indicates that the subject is immunological competent.

In a non-competent mare <1% of the recovered cells in a samples from the endometrium are neutrophils following induction of inflammation. In an immunologic competent mare >2% of recovered cells are neutrophils. These numbers are not specific, but indicate which group the mare of interest could be categorized into.

In an embodiment the invention relates to a method for testing or diagnosing whether a subject is immunological competent, the method comprises the steps of a. providing a composition comprising a compound selected from the group consisting of an anti-dormancy factor, a pro-inflammatory compound, and a resuscitation-promoting factor,
b. administering the composition to the subject,
c. obtaining a sample from the subject, and
d. subjecting the sample to an analysis of determining whether neutrophils are present in the sample.

The composition comprising a compound selected from the group consisting of an anti-dormancy factor, a pro-inflammatory compound, and a resuscitation-promoting factor is further described elsewhere herein.

The method for testing whether a subject is immunological competent may be a step in the method for diagnosing a dormant infection of at least one pathogen in a subject as described herein. The testing for immunologic competence may be performed on the same sample as obtained from the subject when this subject is diagnosed for a dormant infection. Hereby, the sample obtained from the subject when testing for a dormant infection is further subjected to the step of determining whether neutrophils can be visualized in the sample.

The determination whether a subject is immunological competent can be performed within a period of 6 hours to at least 96 hours from the time the composition which should be able to induce an immunological response is administered to the subject. Preferably the determination is performed between 12 h and 84 h from administering the composition. More preferably the determination is performed within 24 h and 72 h. Further preferably the determination is performed within 36 h and 60 h. Most preferably the determination is performed about 48 h after administering the composition to the subject.

Subjects, e.g. mares, can be tested as described above and determined not to be immunological competent and no active infection capable of causing endometritis, vaginitis and/or cervicitis can be observed. It may thus be expected that these subjects have an infection. To proceed with these subjects an aim can be to identify which are the underlying factors that promote the in-competence and try to clear these. Several factors can, however, be relevant here meaning that this may require a number of different tests. Tests for further infections are not described herein, but are known by the person skilled in the art.

An alternative strategy when a subject e.g. a mare is determined to belong to the group of non-immunological competent, as described, is at this time not to try to induce a dormant streptococci or other infection capable of causing endometritis, vaginitis and/or cervicitis. It would be a benefit to wait, for example 2-4 months, and then try again to induce a dormant infection to become active as described herein. At this time the subject e.g. the mare would often have regained her competence to mount an inflammatory response, and the dormant infections are most likely activated if present when the immune response is activated.

In an embodiment the method described herein further comprises a step for re-testing whether the subject is immunological competent and optional performing a diagnosis for a dormant infection, the re-testing method comprises the step of
a. providing a composition comprising a compound selected from the group consisting of an anti-dormancy factor, a pro-inflammatory compound, and a resuscitation-promoting factor,
b. administering the composition to the subject,
c. obtaining a sample from the subject, and
d. subjecting the sample to an analysis of determining the amount of neutrophils present in the sample and
e. optional subjecting said sample to a diagnostic test in order to detect said pathogen, thereby diagnosing said dormant infection,
wherein the re-testing is performed at least two months later than performing a first method for diagnosing a dormant infection of at least one pathogen in a subject, or the re-testing is performed at least two months later than performing a first re-testing.

Activation of a dormant infection is believed to be dependent on the number of resident bacteria and immunological factors associated with the individual subject e.g. mare. Thus in mares with a very heavy infection activation may be set off although the immune function is weak and would not have been enough to support an activation in a less infected mare. It has been observed by the inventors that most mares unable of mounting an immune response/support an activation will also be infected by other bacteria due to a general low resistance towards intruding bacteria from the outer genital tract. These mares are therefore unlikely to get pregnant and should preferably be tested and treated for other infections.

When a mare has a low number of neutrophils and no active infection is observed after treatment with the composition as described herein, this can indicate that the mare is either a normal mare e.g. a young mare who is bred very few times and is capable of removing the inflammatory response very fast. However, the mare may also be non-competent (see above).

When an infection is diagnosed in a mare who is not immunologic competent, a treatment of the infection(s) may comprise uterine lavage and oxytocin. The treatment may be mainly to try to remove any inflammatory debris. However, the effect of the treatment may be minimal, because the mare could be re-infected rapidly after treatment is stopped because the mare is still non-immunologic competent.

A non-immunologic competent uterus is a "tired uterus" that from an immunologic point of view has given up. The immune system of the mare has responded to the situation and "decided" that there is no longer any reason to keep introducing neutrophils into the uterine lumen. Eventually, the best treatment for a mare who is non-immunologic competent is to stop the breeding activities with this mare and thus not further put stress on the uterus. The determination of taking a mare out of the breeding programme can be performed when the mare is tested non-immunologic competent following e.g. two, three or four rounds of tests/diagnosis as described in this section. Each test may be performed at intervals of at least about 2 months, e.g. about 3 months, such as about 4 months to give the mare a possibility to recover from the non-immunologic competent situation of the uterus.

Activation Composition

A composition capable of activating a dormant infection is herein described as an activation composition or induction composition. The term "solution" may be used instead of the term "composition". An activation composition may comprise a compound selected from the group consisting of anti-dormancy factors, pro-inflammatory compounds, and resuscitation-promoting factors. Preferably the activation composition comprises an anti-dormancy factor. More preferably the activation composition comprises a pro-inflammatory compound. Yet further preferably the activation composition comprises a resuscitation-promoting factor.

In the activation composition the pro-inflammatory compound can be selected from the group consisting of spermatozoa, processed spermatozoa, non-viable spermatozoa, IL-1, IL-6, IL-8, TNF-α, leukotrienes, oil emulsions, polymers, alums, saponins, liposomes, ISCOMs (immunostimulating complexes), Lugols iodine, phosphate buffered saline, glycogen, oyster glycogen, *Eschericia coli, Pseudomonas aeruginosa*, lipopolysaccharides, Mycobacterial cell wall components, adjuvants, Freund's complete adjuvant, and Freund's incomplete adjuvant. Preferably the pro-inflammatory compound comprises non-viable spermatozoa. More preferably the non-viable spermatozoa are freeze-damaged or lysed spermatozoa.

In an embodiment the activation composition comprises non-viable spermatoxoa, and the non-viable spermatozoa are present in said composition in an amount of from 1 million to 10 billion spermatozoa cells, such as from 1 million to 100 million, or from 100 million to 200 million, or from 200 million to 300 million, or from 300 million to 400 million, or from 400 million to 500 million, or from 500 million to 600 million, or from 600 million to 700 million, or from 700 million to 800 million, or from 800 million to 900 million, or from 900 million to 1 billion, or from 1 billion to 1.5 billion, or from 1.5 billion to 2 billion, or from 2 billion to 2.5 billion, or from 2.5 billion to 3 billion, or from 3 billion to 3.5 billion, or from 3.5 billion to 4 billion, or from 4 billion to 4.5 billion, or from 4.5 billion to 5 billion, or from 5 billion to 5.5 billion, or from 5.5 billion to 6 billion, or from 6 billion to 6.5 billion, or from 6.5 billion to 7 billion, or from 7 billion to 7.5 billion, or from 7.5 billion to 8 billion, or from 8 billion to 8.5 billion, or from 8.5 billion to 9 billion, or from 9 billion to 9.5 billion, or from 9.5 billion to 10 billion.

In an embodiment the activation composition comprises spermatozoa or non-viable spermatozoa which are from a boar (porcine) or bull (bovine) and/or stallion (equine).

Anti-dormancy factor, pro-inflammatory compound, and/or resuscitation-promoting factor(s) of the composition can be freeze-dried.

The composition can have a volume of from 1 ml to 50 ml, such as from 1 ml to 5 ml, such as from 5 ml to 10 ml, such as from 10 ml to 15 ml, such as from 15 ml to 20 ml, such as from 20 ml to 25 ml, such as from 25 ml to 30 ml, such as from 30 ml to 35 ml, such as from 35 ml to 40 ml, such as from 40 ml to 45 ml, such as from 45 ml to 50 ml.

Preferably the composition is a sterile or aseptic composition.

Further features of the composition (activation composition) are described elsewhere herein. These features can be connected to any of the features mentioned in this section.

The activation composition as described can be used for activation of a dormant infection and the activation composition can thus be used in a method of diagnosis of a condition in a subject. Dormant infections as well as conditions for diagnosis of the infections are described elsewhere herein.

Treatment

Treatment of dormant infection is made difficult or impossible by the dormancy of the infection. Most treatments against infections require active, preferably metabolically active and dividing, microorganisms in order to be effective. This is also the case for lavage, treatment by ecbolic agents and antimicrobial treatment. If one attempts to treat a dormant infection with e.g. the mentioned treatments, there is a high risk that the infection will not be effectively treated, and that the infection will therefore persist even after conclusion of the treatment. This is particularly problematic when combined with the risk of false-negative diagnosis of dormant infections, c.f. herein above. The present inventors have found that dormant infections can be effectively treated by first activating the dormant infection, and then treating the resulting activated infection. Combinations of different treatments will commonly be employed in order to ensure a higher rate of cure. In some cases, it may be sufficient to activate the dormant infection and then let the immune response of the host clear the activated infection without having to actually provide a treatment to the host. This procedure is advantageous because it avoids the extra step of actually treating the host.

Even though a survey of 1149 veterinarians in the United States ranked endometritis as the third most frequently occurring medical problem in adult horses (Traub-Dargatz et al., 1991) no general treatment protocol has been adopted (Liu and Troedsson, 2008). Endometritis in the mare can be caused either by inflammation alone or presence of microorganisms. The constituted treatment aims at reducing the inflammation present by uterine lavage and/or induction of uterine contractions, as well as treatment of the diagnosed microorganism with one or more antimicrobial agent(s).

Uterine lavage is generally performed until the return fluid is clear and without any cellular debris. Total volume used depends on amount of debris/bacteria/PMN's present. Ringer Lactate or 0.9% NaCl is commonly used although other suitable fluids may be used.

Ecbolic agents, like Oxytocin, can be used to stimulate uterine contractions. Oxytocin can for instance be administered to a female horse in an amount of 10-20 iu by intramuscular or intravenous injection. The administration can be performed 4-6 times daily, preferably with a minimum of 4 hours interval. Alternatively, a prostaglandin F2α analogue can be used. Dosage and time interval depends on analogue used. A commonly used analogue is cloprostenol, which can be administered with 250 mg per dose to a female horse. Side effects are minimal if the Ecbolic agent is deposited subcutaneously. It is generally recommended only to use prostaglandins prior ovulation because the corpus luteum, which is formed in the ovary following ovulation, is negatively affected by prostaglandins, even though complete luteolysis is not induced until day 3-5 following ovulation.

A variety of anti-bacterial, anti-fungal and anti-yeast preparations can be used to treat endometritis in the mare. Ideally, the in vitro sensitivity of the isolated organism should be tested before the therapeutic antimicrobial is decided. In most cases the antimicrobial treatment is deposited directly in the uterus, but systemic treatment is also possible. Infections with *Streptococcus* species are most often treated with penicillin, e.g. 5 million iu. in utero for use in a female horse, or related compounds, e.g. ampicillin or ticarcillin (1-3 grams in utero for use in a female horse). If a Gram-negative bacterium such as *E. coli* is isolated, gentamycin (0.5-1 gram in utero for use in a female horse) or another amino glycoside is often used. Cephalosporins, typically third generation, are also used (1 gram in utero for use in a female horse). A comprehensive list of known treatment regimens, including suggestions for anti fungal and anti yeast treatment, can be found in "Manual of Equine Reproduction", by T. L. Blanchard and Colleagues. Dosage of specific compounds should be adjusted to the given host. The skilled person will be able to determine from the relevant literature within the field the applicable dosage regimens.

The available treatments of endometritis are all dependent upon the infection being in an active state. If the pathogenic bacteria are dormant, they will to a very large degree not be affected by treatments by lavage, Ecbolic agents or antimicrobial agents. For this reason, it is highly advantageous to be able to effectively and reliably treat by means of the methods of the present invention.

Treating an activated infection may comprise use of a treatment selected from the group consisting of lavage, administration of an antimicrobial agent, and administration of an ecbolic or contractility increasing compound.

Antibiotics can be used for treatment of endometritis. Antibiotic suggestions for treatment of endometritis can be selected from the group consisting of penicillin, ampicillin, ticarcillin, aminoglycoside, gentamycin, and cephalosporin.

The ecbolic or contractility increasing compound mentioned above may be selected from the group consisting of oxytocin, prostaglandin F2-alpha analogues, cloprostenol. Preferably from the group consisting of oxytocin and prostaglandin F2-alpha analogues.

There are several drugs/pharmaceutical formulations that have ecbolic capabilities—e.g. oxytocin and prostaglandin, but also other drugs. One of the most potent formulations available to induce uterine contractions in the mare is cloprostenol, a prostaglandin F2 alfa analog.

Treatment of endometritis may be performed for at least 6 hours, such as at least 12 hours, for example at least 18 hours, such as at least 24 hours, for example at least 36 hours, such as at least 48 hours, for example at least 72 hours, such as at least 96 hours, for example at least 120 hours, such as at least 144 hours after administration of said composition comprising an anti-dormancy factor to said subject.

Timing of Diagnosis and Treatment in Relation to Estrous Cycle

In one embodiment, the present invention relates to diagnosis or treatment of a dormant infection in a female horse, wherein said dormant infection is capable of causing endometritis. The estrous cycle of the female horse controls when the horse is sexually receptive toward a stallion, and helps to physically prepare the horse for conception. It generally occurs during the spring and summer months, although some horses may be sexually receptive into the late fall. The cycle is controlled by the photoperiod (length of the day). The estrous cycle lasts about 19-22 days, with the average being 21 days. As the days shorten, the horse returns to a period when she is not sexually receptive, known as anestrus.

The estrous cycle generally consists of two phases, the estrus and the diestrus. The estrus, or follicular, phase is 5-7 days in length. During this phase the female horse is in "heat" and is sexually receptive to a stallion. Estrogen is secreted by the follicle during this phase and ovulation occurs in the final 24-48 hours of estrus. The diestrus, or luteal, phase is 14-15 days in length. During this phase the female horse is not sexually receptive to the stallion.

The methods of the present invention can be carried out on a female horse at any time during the estrous cycle or during anestrus. In a preferred embodiment, the method of treatment of the present invention is carried out during estrus. In a preferred embodiment, the method of treatment of the present invention is carried out following activation during or immediately following a period of estrus. In a preferred embodiment, the administering to a female horse of the composition according to the present invention is performed at the first day of estrus, e.g. the initial day of estrus behaviour or e.g. day 15 of the estrous cycle. The sample for diagnostic testing is then taken two days following the administering of the composition, e.g. on day 17 of the estrous cycle. Depending on the diagnostic test employed, the results of the diagnosis will generally be available no later than 2 days after the sampling, e.g. on day 19 of the estrous cycle. In the event of a positive diagnosis, treatment can be initiated on the same day as the diagnostic result is received, e.g. day 19 of the estrous cycle. Depending on the method of treatment, the treatment can be continued for the amount of time necessary, for instance approximately 4-6 days, e.g. until day 3-5 of the following estrous cycle. Breeding or fertilisation of the female horse can take place during treatment or more ideal the breeding can be postponed until the next estrus. If treatment is decided to take place in the following cycle, the activation procedure should preferably be performed 2 days before treatment is initiated. In an embodiment, treatment is performed in the estrus period following the estrus period wherein the diagnosis was performed.

It is advantageous to carry out the methods of the present invention in relation to the estrus phase of the female horse since during this period, breeding horses are handled anyway and performance of the methods can easily be conducted alongside other procedures and tests carried out on the horse. Furthermore, the immune response of the female horse is enhanced during estrus.

Use

The at least one anti-dormancy factor, at least one pro-inflammatory compound, and/or at least one resuscitation-promoting factor described herein above can be used for activating a dormant agent. Preferably the activation of a dormant agent is activation of a dormant infection in a subject.

In an embodiment at least one anti-dormancy factor, at least one pro-inflammatory compound, and/or at least one resuscitation-promoting factor is used for the diagnosis of endometritis, vaginitis and/or cervicitis.

In a further embodiment at least one anti-dormancy factor, at least one pro-inflammatory compound, and/or at least one resuscitation-promoting factor is used for the treatment of endometritis, vaginitis and/or cervicitis.

In a preferred embodiment at least one anti-dormancy factor, at least one pro-inflammatory compound, and/or at least one resuscitation-promoting factor is used for the production of a pharmaceutical composition. Preferably the pharmaceutical composition is suitable for activating a dormant agent. More preferably the pharmaceutical composition is suitable for activating a dormant infection in a subject.

In a further preferred embodiment at least one anti-dormancy factor, at least one pro-inflammatory compound, and/or at least one resuscitation-promoting factor is used for the preparation of a pharmaceutical composition for the diagnosis of endometritis, vaginitis and/or cervicitis.

In another preferred embodiment at least one anti-dormancy factor, at least one pro-inflammatory compound, and/or at least one resuscitation-promoting factor is used for the preparation of a pharmaceutical composition for a process for the treatment of endometritis, vaginitis and/or cervicitis.

In a preferred embodiment at least one anti-dormancy factor, at least one pro-inflammatory compound, and/or at least one resuscitation-promoting factor is used for the preparation of a pharmaceutical composition for improving reproductive success in a female human or female animal.

The at least one anti-dormancy factor, at least one pro-inflammatory compound, and/or at least one resuscitation-promoting factor as mentioned above in this section may be any anti-dormancy factor, pro-inflammatory compound, and/or resuscitation-promoting factor as mentioned elsewhere herein. Other features relating to the anti-dormancy factor, pro-inflammatory compound, and/or resuscitation-promoting factor may also be as mentioned elsewhere herein Preferably the at least one anti-dormancy factor, at least one pro-inflammatory compound, and/or at least one resuscitation-promoting factor are selected from the group of spermatozoa, processed spermatozoa, non-viable spermatozoa, IL-1, IL-6, IL-8, TNF-α, leukotrienes, oil emulsions, polymers, alums, saponins, liposomes, ISCOMs (immunostimulating complexes), Lugols iodine, phosphate buffered saline, glycogen, oyster glycogen, *Eschericia coli*, *Pseudomonas aeruginosa*, lipopolysaccharides, Mycobacterial cell wall components, adjuvants, Freund's complete adjuvant, Freund's incomplete adjuvant, Rpf's and Rpf-like factors, SPS factor.

More preferably the at least one anti-dormancy factor, at least one pro-inflammatory compound, and/or at least one resuscitation-promoting factor comprises non-viable spermatozoa. More preferably the non-viable spermatozoa are freeze-damaged or lysed spermatozoa.

Also preferably composition is aseptic or sterile.

EXAMPLES

Example 1

A first study comprising two consecutive trials and including six brood mares, in this case female horses, was conducted. Each mare was examined clinically prior to the trials and found apparently normal. Bacteriologic culture from an endometrial biopsy as well as exfoliative cytology showed no indications of infection. Inflammation was induced by intrauterine inoculation of $10^9$ E. coli. Bacteriological culture was made from two endometrial biopsies, one from each horn of the uterus. Biopsies were taken before inoculation of the E. coli bacteria, and at 3, 12, 24, 48 and 72 hours post inoculation. Bacteriological culture from the biopsies was performed by standard methods and growth of S. zoo was registered. The entire procedure was repeated two weeks following termination of the first round and after all mares had been treated with intrauterine antibiotics to clear any residual infection from the initial trial.

In the first trial, all mares tested negative for growth of S. zoo prior to inoculation by a definition used under practical circumstances. This means that when five or less S. zoo colonies are detected by culture from a biopsy, the mare was considered negative for infection.

TABLE 2

Trial 1, presence of S. zoo following E. coli inoculation

| Mare | Prior inoculation | 3 h p.i. | 12 h p.i. | 24 h p.i. | 48 h p.i. | 72 h p.i. |
|---|---|---|---|---|---|---|
| 1 | − | − | − | − | − | − |
| 2 | − | − | − | − | − | − |
| 3 | − | − | − | + | − | − |
| 4 | − | − | − | + | − | − |
| 5 | − | − | − | − | − | − |
| 6 | − | − | − | + | − | ++ |

+ indicates presence of bacteria
++ indicates presence of large number of bacteria

TABLE 3

Trial 2, presence of S. zoo following E. coli inoculation

| Mare | Prior inoculation | 3 h p.i. | 12 h p.i. | 24 h p.i. | 48 h p.i. | 72 h p.i. |
|---|---|---|---|---|---|---|
| 1 | − | − | − | − | − | − |
| 2 | + | − | − | − | + | ++ |
| 3 | − | − | − | − | − | − |
| 4 | − | − | − | − | − | ++ |
| 5 | − | − | − | − | * | * |
| 6 | − | − | − | − | − | + |

* This mare was taken out of the trial for intense treatment against E. coli
+ indicates presence of bacteria
++ indicates presence of large number of bacteria Four out of six mares became culture-positive for S. zoo by 24-72 h post inoculation with E. coli. Three of the mares were culture-negative for S. zoo prior to the trials, whereas one mare was barely considered culture-positive (six colonies), for S. zoo at the time of inoculation (trial II).

Using E. coli as an inflammation inducer to activate dormant infections by S. zoo clearly has a potential, but is not ideal as this bacterium establishes an infection on its own lasting at least 48 h. This can make it difficult to recover S. zoo due a massive overgrowth of E. coli. Furthermore, as the E. coli are live organisms, the inflammatory response can be less predictable.

Example 2

A second study including seven mares, in this case female horses, was conducted. Again, all mares were examined clinically and found apparently healthy before initiation of the study. Bacterial culture was made from three different diagnostic specimens from each mare before (time 0), 24, and 48 hours post inflammation induction. Bacterial growth was assessed by culture from an endometrial swab, low volume endometrial flush using 50 ml isotonic saline and an endometrial biopsy. Inflammation was induced by inoculation of $10^9$ dead equine spermatozoa in 10 ml sterile PBS, which had been frozen and thawed prior to inoculation. Before inoculation each sample was tested negative for presence of bacteria, following centrifugation to remove seminal plasma and re-suspension in PBS. Seminal plasma was removed because it has been shown to sometimes down regulate the inflammatory response of the uterus after insemination. Slow freeze-thaw (−18° C.) of spermatozoa without cryoprotectants can induce membrane damage and kill spermatozoa. Killed spermatozoa have an increased ability to induce an inflammatory response in the uterus compared to live sperm. Sterile killed spermatozoa without seminal plasma was therefore used to induce inflammation.

TABLE 4

Presence of S. zoo following induction of inflammation by killed and sterilized stallion spermatozoa

| | 0 h p.i. | | | 24 h p.i. | | | 48 h p.i. | | |
|---|---|---|---|---|---|---|---|---|---|
| Mare | Swab | Flush | Biopsy | Swab | Flush | Biopsy | Swab | Flush | Biopsy |
| 1 | − | − | − | − | − | − | ++ | + | + |
| 2 | − | + | + | + | + | − | − | ++ | − |
| 3 | − | −* | − | − | −* | − | ++ | ++* | ++ |
| 4 | − | − | − | − | ++ | ++* | ++ | ++* | ++ |

TABLE 4-continued

Presence of S. zoo following induction of inflammation by killed and sterilized stallion spermatozoa

| | 0 h p.i. | | | 24 h p.i. | | | 48 h p.i. | | |
|---|---|---|---|---|---|---|---|---|---|
| Mare | Swab | Flush | Biopsy | Swab | Flush | Biopsy | Swab | Flush | Biopsy |
| 5 | − | −* | − | ++ | ++* | − | ++ | ++* | + |
| 6 | − | −* | − | ++ | ++* | ++ | ++ | ++ | ++ |
| 7 | − | −* | − | − | + | − | ++ | ++ | + |

*E. coli was recovered at these sampling points
+ indicates presence of bacteria and
++ indicates presence of large number of bacteria.

All seven mares cultured negative for S. zoo prior to inflammation induction when the traditional swab technique was used, and only mare no. 2 was found culture-positive using the endometrial lavage or biopsy technique. At 24 h p.i. four out of seven (4/7) mares were culture-positive by the swab methods, whereas 5/7 and 2/7 were culture positive by flushing and biopsy, respectively. At 48 h 6/7, 7/7 and 6/7 mares were culture-positive by swab, flushing and biopsy, respectively. The flushing method was apparently slightly more sensitive than the swab and biopsy methods. It is noteworthy, though, that the flushing method was the only method which was positive for E. coli. This could indicate that flushing more readily picks up bacteria, but it could also indicate that this method is more sensitive to contamination from the residing reproductive tract flora during sample collection. Both S. zoo and E. coli are part of the normal bacterial flora in the lower genital tract.

The reason why only two biopsies cultured positive at 24 h p.i., may relate to the very limited area that is included in a biopsy. If the S. zoo infection is localized into discrete areas of the endometrium, a biopsy may have less chance of detecting it.

Visualization of streptococci in the endometrium using fluorescence in situ hybridization (FISH) demonstrated presence of streptococci in four of the seven mares at time 0 h, although streptococci could only be demonstrated by culture from one of the seven mares at this time. These findings demonstrate that the streptococci were present before induction, and not introduced as part of the sampling and/or induction procedure.

Example 3

Maiden Mares

Overall goal: To determine whether dormant streptococci were present in maiden mares, a total of six maiden mares (horses) were evaluated.

Materials and Methods:

Before the initial samples (0 h) the mares were examined by transrectal palpation and ultrasound.

Bacterial culture was performed on all mares using three different techniques—swab, flush and biopsy.

Following sampling all mares were infused in the uterus with the induction solution. Autoclaved spermatozoa (1×10$^9$) were used as induction solution. The induction solution was tested and found microbiological sterile. Two days later (48 h), the six mares were re-evaluated clinically by transrectal palpation and ultrasound, and swab, flush and biopsy samples from the uterus were recovered.

Results and Conclusions:

All mares were found anatomically and clinically normal, but two mares were Diagnosed with a pneumovagina due to poor perineal conformation.

No mares tested positive for any bacteria on samples recovered on time 0 h. Of the six mares one mare tested positive on culture for presence of streptococci (15 colonies). The positive culture was obtained using the flush technique, which appears to be the most sensitive of the three used. The culture positive mare suffered from pneumovagina.

This study indicates that dormant streptococci were not present in the uterus of the tested maiden mares. The results also emphasize the importance of a good perineal conformation in preventing establishment of microorganism in the uterus.

Example 4

Presence of Dormant Streptococci in a Population of Non-Breeding Mares and Problem Mares Overall goal: To determine whether dormant streptococci were present in a population of non-breeding mares and a population of broodmares, non-pregnant even though bred in the breeding season 2009.

Material and Methods:

Evaluated mares (horses) were either non-breeding mares or broodmares. The broodmares were all classified as "problem-mares" e.g. non-pregnant even though they were bred in >2 cycles with a stallion with proven fertility.

Mares were evaluated by transrectal palpation and ultrasonography, and a swab and a low volume flush were performed to evaluate the microbiological status of the mares. Following recovery of the initial sample, termed 0 h, the mares were either infused with 10 ml of PBS or autoclaved spermatozoa (10$^9$) suspended in 10 ml of PBS. Two days/48 h after the initial sampling mares were re-evaluated clinically and swab and low volume flush performed again.

If pathogenic bacteria were isolated from the uterus either on the samples recovered at time 0 h or time 48 h the mares were treated. Treatment consisted of one daily uterine lavage until clear return fluid and 5 days of systemic antibiotics. The antibiotics used are generally considered effective against the isolated bacteria, although this was not tested.

To evaluate treatment efficacy the mares were re-evaluated 3 weeks subsequent termination of treatment. The clinical and microbiological examinations performed and samples recovered were identical to the ones obtained at initiation of the study. Following the initial samples (0 h) all mares were treated with the induction substance (compared to the first set of samples were half of the mares were induced and the other half were not).

Results of Swab Data
Presence of Dormant Streptococci:

| Type of mare | Time (h) | Streptococci determined, No. of mares | Sterile/positive/ Contamination, No. of mares | Total No. of mares |
|---|---|---|---|---|
| Problem | 0 | 1 | 32 | 33 |
| Problem | 48 | 11 | 22 | 33 |
| Non-breeding (SSI) | 0 | 1 | 20 | 21 |
| Non-breeding (SSI) | 48 | 1 | 20 | 21 |

The swab data demonstrate that streptococci (strep) can be isolated from a significantly higher number of mares at time 48 h i.e. after activation of the dormant streptococci compared to time 0 h. All mares P=0.008. Only problem mares P=0.003.

These data demonstrate that dormant streptococci can be found by induction in the group of problem mares, but not in a group of non-breeding mares.

It was tested whether the dormant streptococci were induced by the induction solution or PBS:
Mares selected: Mares sterile at time 0 h and strep isolated at 48 h.
Problem Mares: P=0.01

| Treatment | Strep observed. No. of mares | Sterile/non-strep pathogens/contamination. No. of mares | Total No. of mares |
|---|---|---|---|
| PBS | 1 | 13 | 14 |
| Induction solution | 10 | 9 | 19 |
| Total | 11 | 22 | 33 |

SSI Mares (Non-Breeding Mares): P=1.0

| Treatment | Strep observed. No. of mares | Sterile/non-strep pathogens/contamination. No. of mares | Total No. of mares |
|---|---|---|---|
| PBS | 1 | 10 | 11 |
| Induction solution | 0 | 10 | 10 |
| Total | 1 | 20 | 21 |

All Mares P=0.06

Not included in this experiment were mares from which streptococci were isolated at time 0 h and again at time 48 h. One mare with these findings was present in each of the two groups of mares. In both cases, all mares included were negative at time 0 h. Subsequently, the number of mares becoming positive for strep were 11 and 1 for problem and non-breeding mares, respectively. In case of the problem mares, a significantly higher number of mares become positive for strep when the induction solution is used compared to PBS.

These data demonstrate that more mares are induced using the induction solution (PBS and autoclaved spermatozoa) compared to PBS alone.

If mares from which other bacteria than strep and mares found sterile at time 0 h that changed to strep at 48 h are selected, the numbers are similar to the scenario with sterile mares switching to strep-positive ($P_{problem\ mare}$=0.07, $P_{all\ mares}$=1).

It was also tested whether other pathogens than streptococci could be found at a higher frequency than other bacteria at time 48 h:

| Type of mare | Time (h) | Non-strep pathogens | Sterile/strep/ contamination | Total |
|---|---|---|---|---|
| Problem | 0 | 2 | 31 | 33 |
| Problem | 48 | 2 | 31 | 33 |
| SSI | 0 | 1 | 20 | 21 |
| SSI | 48 | 1 | 20 | 21 |

These data demonstrate that other pathogens than strep are not induced comparing 0 and 48 h. independent of mare type (problem or SSI mares).

Conclusions

Swab data: Streptococci can be dormant in the equine endometrium and can be activated using "the induction solution"

Using the swab test to evaluate endometrial status—mares that change following induction change from sterile to *streptococcus* positive.

In mares sampling negative at 0 h, no other pathogens than strep were isolated at 48 h following induction. This again supports that only Strep are induced but more important that no pathogens are introduced into the uterus during sampling or deposition of "the induction solution".

Low number of mares changing status from sterile (0 h) to contaminated—therefore the procedure is a safe procedure Problem mares (PBS—2 mares, Induction—1 mare)

SSI mares (non)

Minor contamination risk—highly outweighed by advantages

If streptococci are isolated at 48 h following induction then always >10 colonies isolated meaning that the test result is easy to interpret.

Results of Flush Data

Further tests were made to determine whether more strep could be isolated at time 48 h compared to time 0 h compared to other pathogens.

| Type of mare | Time (h) | Strep | Sterile/non-strep pathogens/contamin/strp + *coli* | Total |
|---|---|---|---|---|
| Problem | 0 | 7 | 26 | 33 |
| Problem | 48 | 13 | 20 | 33 |
| SSI | 0 | 2 | 19 | 21 |
| SSI | 48 | 7 | 14 | 21 |

Problem mares: P=0.2, SSI mares: P=0.13, All mares: P=0.03

These data demonstrate that streptococci can be isolated in more mares at time 48 h compared to 0 h. The difference is statistical significant if data from all mares are fused, but not if divided by mare status.

Selected mares: Mares found sterile at time 0 h, mares positive for streptococci at time 0 h and 48 h not included.

Problem Mares Status at 48 h

| Treatment | Strep | Sterile/non-strep pathogens/contamin | total |
|---|---|---|---|
| PBS | 2 | 12 | 14 |
| Induction solution | 4 | 15 | 19 |
| Total | 6 | 27 | 33 |

P = 1.0

SSI Mares Status at 48 h

| Treatment | Strep | Sterile/non-strep pathogens/contamin | total |
|---|---|---|---|
| PBS | 2 | 9 | 11 |
| Induction solution | 2 | 8 | 10 |
| Total | 4 | 17 | 21 |

P = 1.0

These data demonstrate that, when using the flush technique, no difference in the capacity to induce strep can be determined comparing induction solution and control (PBS). Numerically more mares are induced using the induction solution in the group of problem mares but the numbers are too low to demonstrate a significant difference.

The data do not change if mares are selected that are found positive for other bacteria than strep and "sterile mares" are combined and compared to their status at 48 h. Problem mares P=0.73, SSI mares P=1.0

Further tests were made to determine whether other pathogens than strep could be induced following activation or whether more mares could be found positive for other pathogens than strep at 48 h compared to 0 h

| Type of mare | Time (h) | Non-strep pathogens | Sterile/Strep/contamin/ strp + coli | Total |
|---|---|---|---|---|
| Problem | 0 | 7 | 26 | 33 |
| Problem | 48 | 3 | 30 | 33 |
| SSI | 0 | 2 | 19 | 21 |
| SSI | 48 | 1 | 20 | 21 |

All mares: P=0.24, Problem mares: P=0.32, SSI mares: P=1.0

These data demonstrate that no other pathogens increase in numbers comparing time 0 and 48 h.

Further tests were made to determine whether fewer mares would be diagnosed as negative for bacterial infections at time 48 h compared to 0 h. Positive results from these tests would indicate that a dormant infection had been reactivated (induced) by the treatment.

| Type of mare | Time (h) | Sterile | Non-strep pathogens/ Strep/contamin/ strp + coli | Total |
|---|---|---|---|---|
| Problem | 0 | 14 | 19 | 33 |
| Problem | 48 | 6 | 27 | 33 |
| SSI | 0 | 9 | 12 | 21 |
| SSI | 48 | 12 | 9 | 21 |

All mares, P=0.43, SSI mares, P=0.54, Problem-mares, P=0.06

These data demonstrate, if looking at all mares, that the number of mares being culture negative or sterile at 48 h after induction (Induction solution or PBS) is not different compared to 0 h. If only problem mares are evaluated, fewer mares are sterile at 48 h after induction (PBS or induction solution) compared to the status at 0 h (P=0.06, approaching significance). If SSI mares are evaluated there is no difference in the number of mares with a sterile culture at 48 h compared to 0 h.

Compared to the swab results more mares are found positive for strep at 0 h using the flush method. This is the case in 6 mares, 3 in the induced and 3 in the PBS group.

Numbers of Bacteria Isolated Following Induction—Swab and Flush Data

Results

Selected mares: Mares sterile at 0 h and strep isolated at 48 h.

Swab

If Strep isolated following induction always >10 colonies only one mare induced by PBS—between 11-50 colonies isolated Lavage More colonies isolated using the induction solution compared to PBS (low number of mares)

Conclusion of the Flush Data

Strep can be induced, P=0.03, but no difference between PBS or induction solution in inducing capacity at mare level. The flush procedure is much more sensitive than the swab procedure and this may, in part, explain this finding. Furthermore, flushing does imply a higher degree of physical manipulation of the endometrium, which also may help inducing the streps in heavily infected individuals even when just using PBS.

Higher number of bacteria isolated using the induction solution compared to PBS. Low number of positive cases—not statistical significant.

More mares change from sterile to strep (0 h vs. 48 h) in the problem mare group compared to Non-breeding mares (P=0.06).

From 6 mares (3 PBS and 3 Induction) strep were present at 0 h and 48 h. Strep at 0 h and 48 h present once using the swab test. This is likely one of the reason between the two tests, with the swab test being less sensitive than the flush test.

Looking at this from a clinicians point of view trying to get mares pregnant—using this technique gets you closer to the true bacterial status of the endometrium—a key player trying to optimize fertility Sow (Porcine) Data A total of 30 sow uteri were sampled from slaugtherhouse material. The uteri were tested for presence of Streptococci and E. coli using swab technique and biopsy.

| No. | Streptococci | | E. coil | | Sterile |
|---|---|---|---|---|---|
| | <10 | >10 | <10 | >10 | |
| Swab | 6 | — | 7 | 15 | 4 |
| Biopsy | 10 | — | 3 | 16 | 7 |

Most sows are culture-positive

E. coli dominates despite common presence of streptococci

Overall Conclusions from the Experiments
  Streptococci are located deep in the chronically infected uterine epithelia
  Dormant streptococci infections in the equine endometrium can be induced/activated using autoclaved spermatozoa, thereby increasing diagnostic sensitivity and specificity
  Treatment effect following activation still to be evaluated
  Dormant streptococci infections are likely present in the sow.
  By extension, dormant streptococci and/or other bacterial infections may be occur in the human female reproductive tract and, as shown for equines, affect human reproductive efficiency Example 5

Induction of Dormant Streptococci in Mares and Effect of Treatment

Overall goal: To verify presence of dormant streptococci in the uterus of the mare and to examine the effect of two different treatment protocols—standard treatment vs. treatment combined with induction of dormant streptococci
Materials and Methods:
  A total of 36 research mares (horses) were randomly assigned to three treatment groups. The mares were assigned evenly in relation to age.
  The mares were divided in three groups—A: control, $B_1$: induction without treatment and $B_2$: induction with treatment. Autoclaved spermatozoa ($1 \times 10^9$) were used as induction solution.
  Samples (swab, flush and biopsy) were recovered from the mares during estrous using the following scheme:
Cycle one: determination of uterine microbiological status, no induction
Cycle two: Induction performed at time 0 h (group A infused with PBS, group $B_{1+2}$ infused with induction solution) and samples recovered 48 h after induction.
Cycle three: Samples recovered at time 0 h and 48 h in the same estrous period. Group A infused with PBS and group $B_{1+2}$ infused with induction solution at time 0 h.
Cycle four: Treatment cycle. Mares from which bacteria were isolated from the uterus were treated with antibiotics and uterine lavage.
Cycle five: Evaluation of treatment effect. The uterine microbiological status of the treated mares was evaluated.
Results:
  On the initial examinations 30 of the 36 mares were found to be infected in the uterus. This is a very high fraction compared to a standard population of mares. Induction of inflammation with autoclaved spermatozoa did only induce an inflammatory response in 20% of the mares, compared to the expected 100%, which would be the scenario in mares with a normal functioning uterus in relation to immunologic competence.
  Following induction we did not see an increase in cases from which streptococci could be isolated from the uterus. This is unexpected compared to what we have seen before, where streptococci can be induced especially in older mares with a history of uterine infections.
  It is very likely that induction of dormant streptococci were not possible in these mares due to a lack of immune response following induction. We are currently not aware exactly what mechanism/pathway in the immune response is involved in preventing induction of dormant streptococci.

It can be concluded that dormant streptococci can not be induced using autoclaved spermatozoa if an uterine immune response to the induction solution is not mounted by the mare following infusion.

To determine whether a mare can mount an inflammatory response in the uterus, it is necessary to evaluate whether inflammation is initiated following induction of inflammation. This is physically done by determining whether neutrophils (white blood cells) can be visualized in a sample (called exfoliative cytology) recovered from the uterus (swab, biopsy or flush) 48 h after treatment with the pro-inflammatory agent (s). Inflammation in the uterus can be induced using a variety of substances, as described before, therefore use of the induction solution is not the only way to determine whether a mare can mount a uterine inflammatory response or not.

It is known that the induction solution should provoke an inflammatory response in all mares if they are immunological sound/competent in the uterus. In a clinical setting the uterine immunologic status of the mare of interest is not always determined/known. The best way to proceed in the clinical setting may be to attempt to activate/induce dormant streptococci in all mares in which presence of dormant streptococci are suspected, independently of the uterine immunologic status. But, to determine whether the uterus of the evaluated mare is immunologically competent, and therefore potentially able to mount an inflammatory response, it is suggested to evaluate if high numbers of neutrophils can be demonstrated following induction. This is done using exfoliative cytology. If high numbers of neutrophils are found after treatment then the uterus is immunologically competent and dormant streptococci will be activated if present. If none or very few numbers of neutrophils and no streptococci are present 48 h after induction it cannot be ruled out that dormant streptococci are in fact present in the endometrial lining. A common profile of mares that are not immunologically competent in the uterus are mares from which embryo recovery attempts have been performed several times (embryo transfer donor mares) or mares, often older mares, that have been bred in several cycles (>3 cycles), and are still not pregnant. It is therefore a very selected group of mares, and the veterinary clinician managing the mare is, in most scenarios, aware of this. It is therefore a limited number of mares that are not immunologically competent in the uterus, and the vast majority of mares bred using standard protocols are immunologicaly competent in the uterus. A mare that is not immunologically competent will, if no other illness is present, regain uterine immunologic competence in 1-4 months after breeding activities are stopped.

REFERENCES

Alber, J., El-Sayed, A., Lämmler, C., Hassan, A. A., Weiss, R., Zschöck, M. J. Vet. Med. B Infect. Dis. Vet. Public. Health. 2004, 51, 455-458.
ALGHAMDI, A. S., FOSTER, D. N., and TROEDSSON, M. H. T. (2004). Equine seminal plasma reduces sperm binding to polymorphonuclear neutrophils (PMNs) and improves the fertility of fresh semen inseminated into inflamed uteri. J Reprod Fertil 127, 593-600.
Blanchard, T. L. et al, Textbook: "Manual of Equine Reproduction", Mosby 2003.
Boyd, E. H. and Allen, W. R. (1988). Absorption of neomycin from the equine uterus: effect of bacterial and chemical endometritis. Vet Rec 122, 37-39.
Båverud, V., Johanssen, S. K. and Aspan Veterinary Microbiology, 2007, 124, 129-139.

FIALA, S. M., PIMENTEL, C. A., MATTOS, A. L. G., GREGORY, R. M., and MATTOS, R. C. (2007). Effect of sperm numbers and concentration on sperm transport and uterine inflammatory response in the mare. Theriogenology 67, 556-562.

Hafner, L. M., Mcnielly, C. Future Microbiology, 2008, 3, 67-77.

Hinrichs, K., Spensley, M. S., and McDonough, P. L. (1992). Evaluation of progesterone treatment to create a model for equine endometritis. Equine Vet J 24, 457-461.

Keep, N. H., Ward, J. M., Cohen-Gonsaud, M., Henderson, B. Trends in Microbiology, 2006, 14, 271-276.

KOTILAINEN, T., HUHTINEN, M., and KATILA, T. (1994). Sperm-induced leukocytosis in the equine uterus. Theriogenology 41, 629-636

LEE, K. B. and NIWA, K. (2006). Fertilization and Development In Vitro of Bovine Oocytes Following Intracytoplasmic Injection of Heat-Dried Sperm Heads. Biol Reprod 74, 146-152.

Lewis, K. Nature Microbiology Reviews, 2007, 5, 48-56.

Liu, I. K. M. and Troedsson, M. H. T. Theriogenology, 2008, 70, 415-420

Nielsen, J. M. Theriogenology, 2005, 64, 510-518.

Miragaya, M. H., Woods, G. L., and Losinno, L. (1997). Endometritis, salpingitis and fertilisation rates after mating mares with a history of intrauterine lumenal fluid accumulation. Equine Vet J Suppl 25, 109-112.

Nikolapoulos, E. and Watson, E. D. (2000). Effect of infusion volume and sperm numbers on persistence of uterine inflammation in mares. Equine Vet J 32, 164-166.

Ravagnani, A., Finan, C. L. and Young, M. (2005) A novel firmicute protein family related to the actinobacterial resuscitation-promoting factor by non-orthologous domain displacement. BMC genomics, 6:39.

Traub-Dargatz, J. L., Salman, M. D., and Voss, J. L. (1991). Medical problems of adult horses, as ranked by equine practitioners. J Am Vet Med Assoc 198, 1745-1747.

TROEDSSON, M. H. T., DESVOUSGES, A., ALGHAMDI, A. S., DAHMS, B., DOW, C. A., HAYNA, J., VALESCO, R., COLLAHAN, P. T., MACPHERSON, M. L., POZOR, M., and BUHI, W. C. (2005). Components in seminal plasma regulating sperm transport and elimination. Animal Reproduction Science 89, 171-186.

Watson, E. D., Stokes, C. R., and Bourne, F. J. (1988). Concentrations of immunoreactive leukotriene B4 in uterine lavage fluid from mares with experimentally induced and naturally occurring endometritis. J Vet Pharmacol Ther 11, 130-134.

ZERBE, H., SCHUBERTH, H.-J., ENGELKE, F., FRANK, J., KLUG, E., and LEIBOLD, W. (2003). Development and comparison of in vivo and in vitro models for endometritis in cows and mares. Theriogenology 60, 209-223.

The invention claimed is:

1. A method for activating and identifying the presence of a dormant infection of at least one pathogen that is capable of causing at least one infection selected from the group consisting of endometritis, vaginitis, and cervicitis in a mare tested as negative for said at least one pathogen, said method comprising the consecutive steps of:
   a. administering to a mare a composition comprising non-viable spermatozoa without seminal plasma, thereby producing an activated infection in said mare,
   b. obtaining a sample from said mare,
   c. subjecting said sample to a test in order to detect said at least one pathogen,
   thereby identifying the presence of said activated infection, when said at least one pathogen is detected.

2. The method of claim 1, wherein said dormant infection of at least one pathogen is capable of causing endometritis.

3. The method according to claim 1, wherein said dormant infection is caused by a causative agent selected from the group consisting of *Streptococcus equi* subsp. *zooepidemicus, Streptococcus agalactiae, Streptococcus pyogenes, Streptococcus uberis, Streptococcus canis, Streptococcus acidominimus, Escherichia coli, Staphylococcus aureus, Pseudomonas aeruginosa,* and *Chlamydia trachomatis*.

4. The method according to claim 1, wherein said composition is administered to the vagina, cervix and/or uterus of said mare.

5. The method according to claim 1, wherein said mare is undergoing a procedure of in vitro fertilization, assisted fertilization, artificial insemination, or a procedure of breeding.

6. The method according to claim 1, wherein said non-viable spermatozoa are freeze-damaged or lysed spermatozoa.

7. The method according to claim 6, wherein said non-viable spermatozoa are from a boar, bull, or stallion.

8. The method according to claim 1, wherein said composition is administered to said mare by using an insemination technique.

9. The method according to claim 1, wherein said test is selected from the group consisting of: culture, cytology, ultrasound, and PCR.

10. The method according to claim 1, further comprising a step for testing whether said mare is immunologically competent comprising determining the number of neutrophils in said sample.

11. The method according to claim 1, wherein said composition comprising non-viable spermatozoa without seminal plasma is freeze-dried.

12. The method according to claim 1, wherein the composition comprising the non-viable spermatozoa without seminal plasma is sterile.

13. The method according to claim 1, wherein the test is performed 24 to 48 hours after administering the composition.

* * * * *